US011241479B2

(12) United States Patent
Williams

(10) Patent No.: US 11,241,479 B2
(45) Date of Patent: Feb. 8, 2022

(54) TREATMENT METHODS USING BOTULINUM TOXINS

(71) Applicant: PENLAND FOUNDATION, Beaumont, TX (US)

(72) Inventor: Roland M. Williams, Beaumont, TX (US)

(73) Assignee: Penland Foundation, Beaumont, TX (US)

( * ) Notice: Subject to any disclaimer, the term of this patent is extended or adjusted under 35 U.S.C. 154(b) by 0 days.

(21) Appl. No.: 16/995,042

(22) Filed: Aug. 17, 2020

(65) Prior Publication Data

US 2021/0187063 A1 Jun. 24, 2021

Related U.S. Application Data

(63) Continuation of application No. 16/657,950, filed on Oct. 18, 2019, now abandoned.

(51) Int. Cl.

| | |
|---|---|
| *A61K 38/16* | (2006.01) |
| *A61K 38/48* | (2006.01) |
| *A61K 9/00* | (2006.01) |
| *A61P 29/00* | (2006.01) |

(52) U.S. Cl.

CPC .......... *A61K 38/164* (2013.01); *A61K 9/0019* (2013.01); *A61K 38/4893* (2013.01); *A61P 29/00* (2018.01)

(58) Field of Classification Search

None

See application file for complete search history.

(56) References Cited

U.S. PATENT DOCUMENTS

| | | | |
|---|---|---|---|
| 5,766,605 | A | 6/1998 | Sanders et al. |
| 6,063,768 | A | 5/2000 | First |
| 6,139,845 | A | 10/2000 | Donovan |
| 6,632,440 | B1 | 10/2003 | Quinn et al. |
| 6,977,080 | B1 | 12/2005 | Donovan |
| 7,655,244 | B2 | 2/2010 | Blumenfeld |
| 8,734,810 | B2 | 5/2014 | Blumenfeld |
| 9,254,314 | B2 | 2/2016 | Finzi et al. |
| 9,707,207 | B2 | 7/2017 | Finegold |
| 10,011,823 | B2 | 7/2018 | Barbieri et al. |
| 10,258,673 | B2 | 4/2019 | Pokushalov et al. |
| 10,722,552 | B1 | 7/2020 | Williams |
| 2004/0062776 | A1 | 4/2004 | Voet |
| 2004/0220544 | A1 | 11/2004 | Heruth et al. |
| 2005/0147626 | A1 | 7/2005 | Blumenfeld |
| 2005/0191320 | A1 | 9/2005 | Turkel et al. |
| 2007/0259002 | A1 | 11/2007 | Batchelor |
| 2009/0142430 | A1 | 6/2009 | Sanders et al. |
| 2009/0232850 | A1 | 9/2009 | Manack et al. |
| 2010/0303788 | A1 | 12/2010 | Francis et al. |
| 2011/0200639 | A1 | 8/2011 | Blumenfeld |
| 2012/0093827 | A1 | 4/2012 | Van Schaack et al. |
| 2012/0195878 | A1 | 8/2012 | Haag-Molkenteller et al. |
| 2012/0244188 | A1 | 8/2012 | Blumenfeld et al. |
| 2012/0251519 | A1 | 10/2012 | Blumenfeld et al. |
| 2013/0251830 | A1 | 9/2013 | Manack et al. |
| 2015/0086533 | A1 | 3/2015 | Borodic |
| 2017/0173123 | A1 | 6/2017 | Blumenfeld |
| 2017/0333537 | A9 | 11/2017 | Borodic |
| 2018/0071361 | A1 | 3/2018 | Abiad et al. |
| 2019/0038646 | A1 | 2/2019 | Bright et al. |
| 2019/0300583 | A1 | 10/2019 | Jarpe |

FOREIGN PATENT DOCUMENTS

| | | | |
|---|---|---|---|
| EP | 2072039 | A1 | 6/2009 |
| JP | 2012107051 | A | 6/2012 |
| KR | 20100032982 | A | 3/2010 |
| KR | 20150126979 | A | 11/2015 |
| WO | WO 95/28171 | | 10/1995 |
| WO | WO 00/10598 | | 3/2000 |
| WO | WO2010013495 | A1 | 2/2010 |
| WO | WO2011084507 | A1 | 7/2011 |
| WO | WO2014184746 | A1 | 11/2014 |
| WO | WO2019145577 | A1 | 8/2019 |
| WO | WO2020110458 | A1 | 6/2020 |

OTHER PUBLICATIONS

International Search Report arid Written Opinion, PCT/US2020/056206, dated Feb. 1, 2021.

Ryan J. Diel, MD et al., "Photophobia and sensations of dryness in migraine patients occur independent of baseline tear volume and improve following botulinum toxin A injections", HHS Public Access, Br J Ophthalmol. Author manuscript; available in PMC Aug. 1, 2019, pp. 1-15.

Donald C. Rojas, "The role of glutamate and its receptors in autism and the use of glutamate receptor antagonists in treatment", J Neural Transm. Aug. 2014 ; 121(8): 891-905, pp. 1-24.

Juan M. Espinosa-Sanchez et al., "New insights into pathophysiology of vestibular migraine", Frontiers in Neurology, Feb. 2015 | vol. 6 | Article 12, pp. 1-6.

Colleen Doherty, MD, "The Link Between Migraines and Tinnitus, Buzzing or ringing in your ears could be related to your episodes", VeryWell Health, Aug. 6, 2019, pp. 1-13 https://www.verywellhealth.com/link-between-migraines-and-tinnitus-4077631.

(Continued)

*Primary Examiner* — Christina M Borgeest

(74) *Attorney, Agent, or Firm* — Fox Rothschild LLP

(57) ABSTRACT

A method of tolerance to narcotics in a patient in need thereof comprises administering a botulinum toxin to the patient. The botulinum toxin is selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, and a combination thereof. The botulinum toxin may be administered by subcutaneous/intradermal injection. The subcutaneous/intradermal injection may be administered to and/or around the vicinity of a trigeminal nerve, a cervical nerve, a thoracic nerve, a lumbar nerve, and a sacral nerve of the patient. The therapeutically effective amount of the botulinum toxin administered is between about 1 unit and about 150 units.

11 Claims, No Drawings

(56) References Cited

OTHER PUBLICATIONS

Vacca et al., Brain, Behavior, and Immunity 32 (2013) 40-5US-10445799-B20 (Year: 2013).
Fernandez-Rodriguez et al., "Plasma Levels of Substance P in Liver Cirrhosis: Relationship to the Activation of Vasopressor Systems and Urinary Sodium Excretion", Hepatology, Jan. 1995; 21: pp. 35-40,(Year: 1995).
Glatte et al., "Architecture of the Cutaneous Autonomic Nervous System", Frontiers in Neurology, vol. 10, Article 970, Sep. 2019, pp. 1-11, 10: doi: 10.3389/fneur.2019.00970 (Year: 2019).
Web Article: Neuroscience, what-when-how, In Depth Tutorials and Information, Gross Anatomy of the Brain, Dec. 7, 2020, 2 pages, The autonomic system schematic downloaded Nov. 23, 2020 from http://what-when-how.com/neuroscience/the-autonomic-nervous-system-integrative-systems-part-1/; the image is reproduced in the Office action (Year: 2020).
WebMD, ADHD and Dyslexia: How to Tell Them Apart, Dyslexia and ADHD Similarities and Differences, Nov. 30, 2020, 3 pages, The article downloaded Nov. 30, 2020 from https://www.webmd.com/add-adhd/adhd-dyslexia-tell-apart?print=true; 3 pages total (Year: 2020) WebMD.
Chien et al., "Sympathetic Fiber Sprouting in Chronically Compressed Dorsal Root Ganglia Without Peripheral Axotomy", NIH Public Access, Author Manuscript of J. Neuropathic Pain Symptom Palliation. 2005; 1 (1 ): pp. 19-23 (Year: 2005).
Scott and Fryer, "Role of Parasympathetic Nerves and Muscarinic Receptors in Allergy and Asthma", NIH Public Access, Author Manuscript of Chem Immunol Allergy. 2012; 98: pp. 48-69 (Year: 2012).
Web Article, The image downloaded Dec. 4, 2020 from https://nursing-skills.blogspot.com/2014/01/angle-of-injection.html; image reproduced in Office action (Year: 2020.
Dobrek and Thor, "Glutamate NMDA Receptors in Pathophysiology and Pharmacotherapy of Selected Nervous System Dseases", Postepy Hig Med Dosw (online), 2011; 65: pp. 338-346 , 1 Year: 2011).
Erle CH Lim, "Botulinum toxin, Quo Vadis?", Elsevier Ltd., Medical Hypotheses (2007) 69, pp. 718-723 (Year: 2007) http://inti.elsevierhealth.com/ journals/ mehy.
Pugh KR et al., Abstract—"Glutamate and choline levels predict individual differences in reading ability in emergent readers", J.Neurosci. Mar. 12, 2014;34(11):4082-9. doi: 10.1523/JNEUROSCI.3907-13.2014 https://www.ncbi.nlm.nih.gov/pubmed/24623786 (Dec. 13, 2019).
Mayo clinic article, "Autism Spectrum Disorder", Symptoms and Causes, 5 pages (Year: 2019)downloaded on Dec. 23, 2019 from: https://www.mayoclinic.org/diseases-conditions/autism-spectrum-disorder/ symptoms-causes/syc-20352928?p=1.
The Machine Translation of WO2010013495, English Abstract,"Pharmaceutical Composition Containing Highly Purified Botulinum Neurotoxin Therapeutic Agent As Active Ingredient, And Use Thereof", Akaike et al.; Feb. 4, 2010 (Year: 2010).
Nair et al., "Impaired Thalamocortical Connectivity In Autism Spectrum Disorder: A Study Of Functional And Anatomical Connectivity", Brain, Journal of Neurology, 2013; 136: 1942-1955 (Year: 2013).
Panju et al., "Atypical Sympathetic Arousal In Children With Autism Spectrum Disorder And Its Association With Anxiety Symptomatology", Molecular Autism (2015) 6:64, pp. 1-10 (Year: 2015).
Saunte et al., "Improverment In Reading Symptoms Following Botulinwn Toxin A Injection For Convergence Insufficiency Type Intermittent Exotropia", Acta Ophthalmologica (1755375X). Aug. 2015, vol. 93 Issue 5, pp. 1-3 (Year: 2015).
The WebMD website, "Treatments for Dyslexia", The International Dyslexia Association. National Center for Learning Disabilities. National Center for Neurological Disorders and Stroke, https://www.webmd.com/children/dyslexia-treatments; accessed Jun. 22, 2020 , 1 page, (Year: 2020).
Hulme et al., "Reading Disorders And Dyslexia", Current Opinion Pediatrics2016, 28: pp. 731-735 (Year: 2016) www.co-pediatrics.com.
Mazzone et al., "Vaginal Afferent Innervation Of The Airways In Health And Disease", Physiol Rev 96: 975-1024, 2016, pp. 975-1024, (Year: 2016).
Schematic of innervation of organs, available from https://ars.els-cdn.com/content/image/3-s2.0-B9780323378048000055-f005-001-9780323378048.jpg, downloaded Jun. 22, 2020 and reproduced within the Office action (Year: 2020).
The Harvard Medical School , "Cardiac Arrhythmias", Harvard Health Publishing, Published Feb. 2019, website downloaded Jul. 18, 2020 from: https://www.health.harvard.edu/a_to_z/cardiac-arrhythmias-a-to-z; 5 pages total (Year: 2020).
Machine English Translation of the foreign patent document, KR20100032982, 7 pages total (Year: 2010).
Mitchell and Borasio et al., "Amyotrophic Lateral Sclerosis", Seminar, Lancet 2007; vol. 369: 2 pp. 2031-2041 (Year: 2007).
Oomens and Forouzanfare t al., "Pharmaceutical Management of Trigeminal Neuralgia in the Elderly", Review Article Drugs Aging (2015) 32: pp. 717-726 (Year: 2015).
S. Kumar, "The Emerging Role Of Botulinum Toxin In The Treatment Of OroFacial Disorders: Literature Update", Asian Journal Pharm Clin Res, vol. 10, Issue 9, 2017, pp. 21-29 (Year: 2017).
Lewitt and Trosch, et al., "Idiosyncratic Adverse Reactions to Intramuscular Botulinum Toxin Type A Injection", Movement Disorders, 1997; 12: pp. 1064-1067 (Year: 1997).
Squires et al., "The Use of Botulinum Toxin Injections to Manage Drooling in Amyotrophic Lateral Sclerosis/Motor Neurone Disease: A Systematic Review", Dysphagia (2014) 29: pp. 500-508 (Year: 2014).
The website downloaded on Jul. 2, 2020 from Juvenile Amyotrophic Lateral Sclerosis,Genetic and Rare Diseases Information Center (GARD)—an NCATS Program, https://rarediseases.info.nih.gov/diseases/11901/juvenile-amyotrophic-lateral-sclerosis; Jul. 2, 2020, 8 pages total (Year: 2020).
Mortazavi et al., "Xerostomia Due to Systemic Disease: A Review of 20 Conditions and Mechanisms", Ann Med Health Sci Res. Jul.-Aug. 2014; 4(4): 503-510. doi: 10.4103/2141-9248.139284: 10.4103/2141-9248.139284 (Year: 2014).
The website downloaded Jul. 21, 2020 from Children's Hospital of Pittsburgh , "Cirrhosis in Children: Symptoms and Treatment", UPMC, 4 pages total . Jul. 21, 2020 (Year: 2020) (https://www.chp.edu/our-services/transplant/liver/ education/liver-disease-states/cirrhosis.
Frank CT Smith, "Hyperhidrosis", Vascular Surgery—II, 2013; 31: pp. 251-255; doi: https://doi.org/10.1016/j.mpsur.2013.03.005 (Year: 2015).

TREATMENT METHODS USING BOTULINUM TOXINS

CROSS-REFERENCED TO RELATED APPLICATION

This application is a continuation of U.S. patent application Ser. No. 16/657,950 filed Oct. 18, 2019. The entirety of prior application is expressly incorporated herein by reference thereto.

FIELD OF THE INVENTION

The present invention generally relates to methods for diagnosing and treating (including alleviating and/or preventing) neuropsychiatric and/or neurological disorders, including Dry Eye Syndrome (DES), ASD (autism), tolerance to narcotics, vestibular vertigo and tinnitus.

BACKGROUND OF THE INVENTION

Botulinum toxins cleave and destroy a protein called synaptosomal nerve-associated protein 25 ("SNAP25") and/or synaptobrevin (also called vesicle-associated membrane protein ("VAMP")). Botulinum toxins A, C and E cleave SNAP25 at different locations, but the effect is the same—the protein is destroyed and cannot function until the cell makes new ones. Botulinum toxins B, D, F and C cleave VAMP present at the cytoplasmic surface of the synaptic vesicle. The two important locations in the body where they are found are at the terminals of the motor neurons (muscle) and in the cell membranes of astrocytes, glial cells, and satellite cells. These three cell types surround sensory neurons and form part of the blood-brain barrier. In motor nerves, to cause them to fire, vesicles of acetylcholine are moved from inside the motor neuron across the cell membrane at the synapse between the motor nerve and muscle fiber. Acetylcholine is released into the synapse and activated receptors in the muscle fiber cause it to contract. In sensory nerves, when a nerve is damaged from physical or mental injuries, the three aforementioned structural cells produce large amounts of substance P, Calcitonin Gene Related Peptide (CGRP), and glutamate internally and it is moved by vesicles to the cell membrane where the SNAP25 and/or VAMP moves it through the cell membrane and releases it into the cerebral spinal fluid that surrounds the neurons. There it binds to the receptor on the sensory nerves, causing the neuroexcitatory effects. It can also diffuse in the cerebral spinal fluid (CSF) and influence other sensory nerves to become hyperactive, a process called central sensitization.

This mechanism of cleaving the SNAP25 and/or VAMP in muscles and sensory nerves causes the only known clinical effects of botulinum. It paralyzes muscles for 3-4 months until the cell grows a new protein. This effect has been used for decades for overactive muscles (cervical dystonia, blepharospasm, tic, Parkinson's, cerebral palsy, etc.), wrinkles in the face, excessive sweating, and overactive bladder.

In the sensory nerves it has been used for migraines and depression. The effect of blocking the SNAP25 and/or VAMP in the glial, satellite, and astrocyte cells will work for 5-9 months until these cells grow their new proteins. The important part of this is the botulinum effect does not destroy cells and does not stop the normal production of or effects of acetylcholine (muscles) or substance F, CGRP, or glutamate in sensory nerves. These facts give huge advantages over a monoclonal antibody which would eliminate all glutamate, CGRP and substance P. Side effects would be disastrous. The receptor antagonists also have problems. They are not site-specific; they block glutamate, substance P and CGRP everywhere. Too little glutamate, substance P, and CGRP is a problem as well as too much. It is hard to regulate the oral or I.V. doses to obtain the correct reduction in areas that are too high in glutamate, substance P, and CGRP, without over reduction in areas with normal levels.

The cleaving of the SNAP25 and/or VAMP allows small doses of botulinum toxin to be injected into specific muscles to calm their overreaction or paralyze them temporarily if that is desired. Or, if injected subcutaneously near unmyelinated sensory nerves, it can stop the overproduction of the sensory neuroexcitatory compounds without affecting normal glutamate, substance P, and CGRP production and function. It is, however, noted that botulinum toxin is highly lethal. It is the most toxic poison known. One molecule of botulinum toxin destroys one protein molecule of SNAP25 and/or VAMP. A little bit goes a long way. It's production, storage and injection must be done with knowledge and care.

In particular, the mechanism of the sensory effect (stopping overproduction of glutamate, substance P, and CGRP) is as follows. Almost all nerves in the human body are surrounded by a protective coating called myelin. It protects the nerve and makes neural conduction faster. Botulinum toxin has difficulty penetrating the myelin. Just, under the skin are some sensory pain nerves called C-fibers, which are unmyelinated. Research has shown that botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess substance P, CGRP, and glutamate, that is involved in the neural injury response mechanism without affecting normal glutamate, substance P, and CGRP production, use, or receptors. An example of what goes wrong with the normal nerve mechanism is an infection of a nerve by the shingles virus. The infection damages the nerve, but does not kill it, or there would be no feeling (numbness). This causes a spike in the production of glutamate, substance P, and CGRP. This causes the well-known shingles pain and hypersensitivity. Over 2-3 months the infection is controlled, the nerve heals, and the overproduction of the neuroexcitatory chemical gets back to normal. However, sometimes, for unknown reasons, the overproduction does not get back to normal but remains high and the severe chronic pain and hypersensitivity persists. Chronically overstimulated neurons can cause numerous problems depending on where they are located. The neuroexcitatory chemicals can travel up the spinal cord to the brain in the CSF and affect neurons there. This process is called central sensitization. Depending on where it is produced and where it travels to, it can cause chronic pain, headaches, vertigo, sensitivity to light, sensitivity to touch, cold sensitivity, overactive bladder, depression, anxiety, flashbacks, mental fogginess, vasoconstriction of extremities, sleep disturbances, and perhaps the death and malformation of the developing neural architecture in children with ASD (autism).

SUMMARY OF THE INVENTION

The claimed invention relates to a method of treating dry eye syndrome in a patient in need thereof. The method comprises administering a botulinum toxin to the patient. The botulinum toxin may be administered by subcutaneous/ intradermal injection. The subcutaneous/intradermal injection may be administered to and/or around the vicinity of a trigeminal nerve of the patient. The trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof. The subcutaneous/intradermal injection may be administered to and/or around the vicinity of a cervical nerve of the patient. The cervical nerve is selected from the group consisting of a c-2 nerve, c-3 nerve, c-4 nerve, c-5 nerve, c-6 nerve, c-7 nerve, c-8 nerve and a combination thereof. In some embodiments, the subcutaneous/intradermal injection may be administered to and/or around the vicinity of a trigeminal nerve and a cervical nerve of the patient. Preferably, the administering for an adult comprises 2-4 units to and/or around the vicinity of an ophthalmic, maxillary, and/or mandibular nerve of the trigeminal nerve (bilateral) and/or 2-4 units to and/or around the vicinity of c-2 to c-3, c-4 to c-6, and/or c-7 to c-8 of the cervical nerve, about one-inch lateral to the spine (bilateral). The administering for a toddler about from 1 to 5 years old is adjusted for age and weight. In some desirable embodiments, the botulinum toxin is selected from the group consisting of botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, and a combination thereof. The botulinum toxin can be used with other modulating drugs or chemicals. In further embodiments, the therapeutically effective amount of the botulinum toxin administered is between about 1 unit and about 150 units.

The claimed invention is also related to method of treating ASD (autism) in a patient in need thereof. The method comprises administering a botulinum toxin to the patient. The botulinum toxin may be administered by subcutaneous/intradermal injection. The subcutaneous/intradermal injection may be administered to and/or around the vicinity of a trigeminal nerve of the patient. The trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, interior alveolar nerve, mental nerve, an auriculotemporal nerve, lesser occipital nerve, a greater occipital nerve and a combination thereof. The subcutaneous/intradermal injection may be administered to and/or around the vicinity of a cervical nerve of the patient. The cervical nerve is selected from the group consisting of a c-2 nerve, c-3 nerve, c-4 nerve, c-5 nerve, c-6 nerve, c-7 nerve, c-8 nerve and a combination thereof. In some embodiments, the subcutaneous/intradermal injection may be administered to and/or around the vicinity of a trigeminal nerve, a thoracic nerve, a lumbar nerve, and a sacral nerve of the patient. In some other embodiments, trigeminal nerve, a cervical nerve, a thoracic nerve, a lumbar nerve, and a sacral nerve of the patient. Preferably, the administering for an adult comprises by subcutaneous/intradermal injection 2-4 units to and/or around the vicinity of an ophthalmic, maxillary, and/or mandibular nerve of the trigeminal nerve (bilateral), 2-4 units to and/or around the vicinity of c-2 to c-3, c-4 to c-6, and/or c-7 to c-8 of the cervical nerve, about one-inch lateral to the spine (bilateral), 2-4 units to and/or around the vicinity of t-2 to t-3, t-5 to t-6, t-7 to t-9, and/or t-10 to t-12 of the thoracic nerve, about one inch lateral to the spine (bilateral), 2-4 unit to and/or around the vicinity of 1-1 to 1-2, 1-2 to 1-3, and/or 1-4 to 1-5 of the lumbar nerve, about one inch lateral to the spine (bilateral), and/or 2-4 units to and/or around the vicinity of s-1 to s-2, s-3 to s-4, and/or s-4 to s-5 of the sacral nerve, about one inch lateral to the spine (bilateral). The administering for a toddler about from 1 to 5 years old is adjusted for age and weight. In some desirable embodiments, the botulinum toxin is selected from the group consisting of botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, and a combination thereof. In further embodiments, the therapeutically effective amount of the botulinum toxin administered is between about 1 unit and about 150 units. In infants or toddlers from about 1 to 5 year olds, it is used to prevent or minimize damage to the developing brain; in older children and adult Autism Spectrum Disorder (ASD) patients, it will be used to reduce or eliminate their symptoms.

The claimed invention is also related to method of treating tolerance to narcotics in a patient in need thereof. The method comprises administering a botulinum toxin to the patient. The botulinum toxin may be administered by subcutaneous/intradermal injection. The subcutaneous/intradermal injection may be administered to and/or around the vicinity of a trigeminal nerve of the patient. The trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof. The subcutaneous/intradermal injection may be administered to and/or around the vicinity of a cervical nerve of the patient. The cervical nerve is selected from the group consisting of a c-2 nerve, c-3 nerve, c-4 nerve, c-5 nerve, c-6 nerve, c-7 nerve, c-8 nerve and a combination thereof. In some embodiments, the subcutaneous/intradermal injection may be administered to and/or around the vicinity of a trigeminal nerve, a thoracic nerve, a lumbar nerve, and a sacral nerve of the patient. In some other embodiments, trigeminal nerve, a cervical nerve, a thoracic nerve, a lumbar nerve, and a sacral nerve of the patient. Preferably, the administering for an adult comprises by subcutaneous/intradermal injection 2-4 units to and/or around the vicinity of an ophthalmic, maxillary, and/or mandibular nerve of the trigeminal nerve (bilateral), 2-4 units to and/or around the vicinity of c-2 to c-3, c-4 to c-6, and/or c-7 to c-8 of the cervical nerve, about one-inch lateral to the spine (bilateral), 2-4 units to and/or around the vicinity of t-2 to t-3, t-5 to t-6, t-7 to t-9, and/or t-10 to t-12 of the thoracic nerve, about one inch lateral to the spine (bilateral), 2-4 unit to and/or around the vicinity of 1-1 to 1-2, 1-2 to 1-3, and/or 1-4 to 1-5 of the lumbar nerve, about one inch lateral to the spine (bilateral), and/or 2-4 units to and/or around the vicinity of s-1 to s-2, s-3 to s-4, and/or s-4 to s-5 of the sacral nerve, about one inch lateral to the spine (bilateral). These are adult dosages. The dosage for 0-5 year olds would have to be adjusted for age and weight. In some desirable embodiments, the botulinum toxin is selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof and a combination thereof. In further embodiments, the therapeutically effective amount of the botulinum toxin administered is between about 1 unit and about 150 units.

The claimed invention relates to a method of treating vestibular vertigo in a patient in need thereof. The method comprises administering a botulinum toxin to the patient. The botulinum toxin may be administered by subcutaneous/intradermal injection. The subcutaneous/intradermal injection may be administered to and/or around the vicinity of a trigeminal nerve of the patient. The trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof. The subcutaneous/intradermal injection may be administered to and/or around the vicinity of a cervical nerve of the patient. The cervical nerve is selected from the group consisting of a c-2 nerve, c-3 nerve, c-4 nerve, c-5 nerve, c-6 nerve, c-7 nerve, c-8 nerve and a combination thereof. In some embodiments, the subcutaneous/intradermal injection may be administered to and/or around the vicinity of a trigeminal nerve and a cervical nerve of the patient. Preferably, the administering for an adult comprises 2-4 units to and/or around the vicinity of an ophthalmic, maxillary, and/or mandibular nerve of the trigeminal nerve (bilateral) and/or 2-4 units to and/or around the vicinity of c-2 to c-3, c-4 to c-6, and/or c-7 to c-8 of the cervical nerve, about one-inch lateral to the spine (bilateral). The administering for a toddler about from 1 to 5 years old is adjusted for age and weight. In some desirable embodiments, the botulinum toxin is selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, and a combination thereof. In further embodiments, the therapeutically effective amount of the botulinum toxin administered is between about 1 unit and about 150 units.

The claimed invention relates to a method of treating tinnitus in a patient in need thereof. The method comprises administering a botulinum toxin to the patient. The botulinum toxin may be administered by subcutaneous/intradermal injection. The subcutaneous/intradermal injection may be administered to and/or around the vicinity of a trigeminal nerve of the patient. The trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, interior alveolar nerve, mental nerve, an auriculotemporal nerve, lesser occipital nerve, a greater occipital nerve and a combination thereof. The subcutaneous/intradermal injection may be administered to and/or around the vicinity of a cervical nerve of the patient. The cervical nerve is selected from the group consisting of a c-2 nerve, c-3 nerve, c-4 nerve, c-5 nerve, c-6 nerve, c-7 nerve, c-8 nerve and a combination thereof. In some embodiments, the subcutaneous/intradermal injection may be administered to and/or around the vicinity of a trigeminal nerve and a cervical nerve of the patient. Preferably, the administering for an adult comprises 2-4 units to and/or around the vicinity of an ophthalmic, maxillary, and/or mandibular nerve of the trigeminal nerve (bilateral) and/or 2-4 units to and/or around the vicinity of c-2 to c-3, c-4 to c-6, and/or c-7 to c-8 of the cervical nerve, about one-inch lateral to the spine (bilateral). The administering for a toddler about from 1 to 5 years old is adjusted for age and weight. In some desirable embodiments, the botulinum toxin is selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, and a combination thereof. In further embodiments, the therapeutically effective amount of the botulinum toxin administered is between about 1 unit and about 150 units.

The claimed invention is also related to a method of treating anxiety and/or depression in a patient in need thereof. The method comprises diagnosing anxiety and/or depression by a symptom and a blood glutamate level of the patient; administering a botulinum toxin to the patient. The symptom is selected from the group consisting of changes in sleep, appetite, energy level, concentration, daily behavior or self-esteem, thoughts of suicide, and combinations thereof. Psychological evaluation and medical testing may be used to determine whether the diagnosis of anxiety and/or depression is due to physical injury or due to a psychological state of the patient. In some embodiments, the diagnosis further comprises psychoanalysis. The method may further comprise a step of providing the patient with mental therapy if the patient has experienced mental injury or trauma. In some other embodiments, the diagnosis further comprises medical examination. The method may further comprise a step of providing the patient with medical treatment if the patient has suffered medical injury. If all the symptoms are not relieved after administering botulinum toxin, an antidepressant may be administered to the patient. The method comprises administering a botulinum toxin to the patient. The botulinum toxin may be administered by subcutaneous/intradermal injection. The subcutaneous/intradermal injection may be administered to and/or around the vicinity of a trigeminal nerve of the patient. The trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof. The subcutaneous/intradermal injection may be administered to and/or around the vicinity of a cervical nerve of the patient. The cervical nerve is selected from the group consisting of a c-2 nerve, c-3 nerve, c-4 nerve, c-5 nerve, c-6 nerve, c-7 nerve, c-8 nerve and a combination thereof. In some embodiments, the subcutaneous/intradermal injection may be administered to and/or around the vicinity of a trigeminal nerve, a thoracic nerve, a lumbar nerve, and a sacral nerve of the patient. In some other embodiments, trigeminal nerve, a cervical nerve, a thoracic nerve, a lumbar nerve, and a sacral nerve of the patient. Preferably, the administering for an adult comprises by subcutaneous/intradermal injection 2-4 units to and/or around the vicinity of an ophthalmic, maxillary, and/or mandibular nerve of the trigeminal nerve (bilateral), 2-4 units to and/or around the vicinity of c-2 to c-3, c-4 to c-6, and/or c-7 to c-8 of the cervical nerve, about one-inch lateral to the spine (bilateral), 2-4 units to and/or around the vicinity of t-2 to t-3, t-5 to t-6, t-7 to t-9, and/or t-10 to t-12 of the thoracic nerve, about one inch lateral to the spine (bilateral), 2-4 unit to and/or around the vicinity of 1-1 to 1-2, 1-2 to 1-3, and/or 1-4 to 1-5 of the lumbar nerve, about one inch lateral to the spine (bilateral), and/or 2-4 units to and/or around the vicinity of s-1 to s-2, s-3 to s-4, and/or s-4 to s-5 of the sacral nerve, about one inch lateral to the spine (bilateral). The administering for a toddler about from 1 to 5 years old is adjusted for age and weight. In some desirable embodiments, the botulinum toxin is selected from the group consisting of botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, and a combination thereof. In further embodiments, the therapeutically effective amount of the botulinum toxin administered is between about 1 unit and about 150 units.

DETAILED DESCRIPTION OF THE PREFERRED EMBODIMENTS

Further in relation to this, before explaining at least the preferred embodiments of the invention in greater detail, itis to be understood that the invention is not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term “about” means approximately or nearly and in the context of a numerical value or range set forth herein means ±10% of the numerical value or range recited or claimed.

The term “treating” includes partially or completely delaying, alleviating, mitigating or reducing one or more disorders or conditions incidental symptoms and/or to mitigate, alleviate or blocking disorder or condition one or more causes. Treatment under the claimed invention may be a preventative treatment, prophylactic treatment, remission of treating or ameliorating treatment.

The term “therapeutically effective amount” or “therapeutically effective dose” refers to the amount of a composition, compound, therapy, or course of treatment that, when administered to an individual for treating a disorder or disease, is sufficient to effect such treatment for the disorder or disease. The “therapeutically effective amount” will vary depending on the composition, the compound, the therapy, the course of treatment, the disorder or disease and its severity and the age, weight, etc., of the individual to be treated.

The term “unit” refers to the amount of botulinum toxin needed to kill 50% of a group of 18-20 gm female swiss-webster mice given the injection intraperitoneally.

The term “vicinity of a nerve” refers to anywhere on the dermatome involved with the nerve.

In accordance with the principles of the present invention, use of botulinum toxin to treat a variety of symptoms is provided.

Treatment of Dry Eye Syndrome

Dry Eye Syndrome (DES), also known as keratoconjunctivitis sicca (KCS), is a condition that forms when the eyes do not produce enough tears, the tears evaporate too quickly, or the eyes do not produce the correct type of tears or tear film. Tear film is what is spread over the eyes when we blink, and is composed of three layers—an inner, mucus-like layer, a middle watery layer, and an outside oily layer. The inner, mucin layer nourishes the cornea and helps tears stick to the eye surface. Much of the mucin is secreted by specialized goblet cells in the conjunctival epithelium. The middle water or aqueous layer helps prevent infection and wash away particles. Most aqueous fluid is secreted from the lacrimal glands. The outside oil or lipid layer, mostly secreted from the meibomian glands, seals the film to reduce evaporation of natural tears. DES can cause damage and discomfort to the ocular surface and is characterized by inflammation and gland dysfunction. Causes of this condition vary greatly and include environmental conditions, inflammatory diseases, hormonal imbalances, systemic disorders (such as diabetes, lupus, rheumatoid arthritis, Sjogren’s syndrome, etc.), eye surgery, and medication hypersensitivity. This application focuses on a portion of these causes that have the potential for specific resolution.

95% of patients who have had LASIK eye surgery experience postsurgical DES. One month after surgery, 60% of patients still suffer from DES. Although the majority of patients improve after 6-12 months, 30% are referred to ophthalmologists for chronic dry eye. 9% of patients who have had cataract eye surgery develop chronic dry eye, and 60% have it initially.

The incisions in the cornea of the eye in these types of procedures result in severing branches of the long ciliary nerves, which are branches of the ophthalmic division of the trigeminal nerve. These nerves supply the sensory innervation of the cornea. The greater petrosal nerve, which is a branch of the facial nerve, supplies the innervation of the lacrimal gland. There is a lot of anastomosis (interconnection) between the facial and trigeminal nerves in this area. A study has shown that nonsurgically induced DES is much more common in people with neuropathic conditions such as migraines and fibromyalgia.

As previously mentioned, when sensory nerves are injured, in this case by surgical incision, they produce excess glutamate, substance P, and calcitonin gene-related peptide (CGRP). The cutting and damage to the corneal sensory nerves stimulate the overproduction of these substances, which results in hypersensitivity in the cornea. This stimulation affects the lacrimal glands by suppressing tear production causing the pain and hypersensitivity as in the aforementioned example of shingles. The long ciliary nerve gets hypersensitized by the produced glutamate, substance P, and CGRP, which causes pain. Dryness causes further irritation due to the glutamate, substance P, and CGRP effects on the glands producing the different tear layer. The excess production of glutamate, substance P, and CGRP slows and normalizes eventually as the eye heals. In some people, however, this overproduction does not return to normal with time as it should, resulting in consistent chronic overproduction of the neuroexcitatory chemicals, and chronic dry eye syndrome results.

In people with chronic neuropathic conditions such as migraines, fibromyalgia, and facial post-shingles pain syndrome, the excess glutamate, substance and CGRP may be from the chronic overproduction of these chemicals which spread from other sensory nerves by a process called central sensitization. This sensitization effects the long ciliary nerve and the facial nerves that innervate the lacrimal glades, goblet cells, and meibomian glands. The excess neuroexcitation from other nerves affects the corneas and lacrimal glands in the same way a surgical injury does, resulting in a state of chronic overstimulation of the involved nerves.

To diagnose DES, blood glutamate levels could be checked at regular doctor visits. Physical symptoms could be also checked. They may include, but not be limited to, a) a stinging, burning or scratchy sensation in your eyes, b) stringy mucus in or around your eyes, c) sensitivity to slight, d) eye redness, e) a sensation of having something in your eyes, f) difficulty wearing contact lenses, g) difficulty with nighttime driving, h) watery eyes, and i) blurred vision or eye fatigue.

If a patient is diagnosed to experience DES after eye surgeries such as LASIK surgery or cataract surgery, they can be given botulinum toxin subcutaneously or by any other injection that allows the botulinum toxin to reach the unmyelinated sensory C fiber (e.g., intradermal injection, etc.) to prevent or alleviate related symptoms and/or blood tests to assess blood levels of substance P, CGRP, and glutamate. The botulinum toxin injection can be given to and/or around the vicinity of a trigeminal nerve and/or a cervical nerve of the patient. The trigeminal nerve may include, but not be limited to, an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The cervical nerve may include, but not be limited to, a c-2 nerve, c-3 nerve, c-4 nerve, c-5 nerve, c-6 nerve, c-7 nerve, c-8 nerve and a combination thereof. For example, 2-4 units to and/or around the vicinity of an ophthalmic, maxillary, and/or mandibular nerve of the trigeminal nerve (bilateral) and/or 2-4 units to and/or around the vicinity of c-2 to c-3, c-4 to c-6, and/or c-7 to c-8 of the cervical nerve, about one-inch lateral to the spine (bilateral) can be administered. The bilateral injections are necessary even if the dry eye syndrome is in one eye because there is substantial crossover side to side in the trigeminal and cervical nerves. These are adult dosages. The dosage for 0-5 year olds would have to be adjusted for age and weight. Botulinum toxin is given to lower the levels of substance P CGRP, and glutamate, and it normally begins to work after about three days. It normally takes for botulinum toxin about one to two weeks to reach the height of its effectiveness. When the botulinum toxin wears off and blood tests show an increase in substance P, glutamate, or CGRP, the symptoms begins to redevelop, and more botulinum toxin can be given to combat this effect. If levels/symptoms fail to normalize, then if desired, a small dose of one of the glutamate antagonists can be administered to help lower glutamate levels without producing side effects.

In general, the therapeutically effective dosage or amount can be between 1-150 units depending on their body weights. The dosage for adults whose weight is about 150 lbs. is about 50-150 units. For children over about 5 year olds at which brain formation has ceased, the dosage can be adjusted to their body weight. For example, for infants or toddlers (from about 1 to 5 year olds), the dosage can be about 1-30 units.

Treatment of Autism

Autism is a developmental disorder characterized by difficulties with social interaction, communication, and by restricted and repetitive behavior. Parents usually notice signs during the first 2-3 years of their child's life. These signs often develop gradually, though some children with autism reach their expected developmental milestones at a normal pace before worsening. The cause is unknown, But it seems to be associated with a combination of genetic and environmental factors. Risk factors during pregnancy include certain infections, such as measles and toxins, including valproic acid, alcohol, cocaine, pesticides, and air pollutants. Controversies surround other proposed environmental causes, for example, the vaccine hypothesis, which has been disproved. Autism affects information processing in the brain by altering how nerve cells and their synapses connect and organize. The mechanism is not entirely understood. The DSM-5, autism, and less severe forms of the condition, including Asperger syndrome and pervasive developmental disorders not otherwise specified (PDD-NOS), have been combined into the diagnosis of Autism Spectrum Disorder (ASD).

As previously mentioned, the exact cause of ASD (autism) is unknown. No genetic abnormalities are found in roughly 90% of cases. In the remaining 10%, genetic mutations have been found, and almost all of these are related to glutamate receptors or the way glutamate is metabolized. There is no animal model for autism; it is only a human condition. The reason for this is because, in a neural capacity, it is a lack of formation of or damage to the developing parts of the brain that are only found in the human brain. From approximately age 1.5 to 5 years, these special structures and the complex neural network around and between them organize and grow. The neurons connect in a complex, mesh-like pattern. Special slender, tapered neurons (VENs) are involved with empathy, guilt, embarrassment, etc., and are higher functioning structures only humans and great apes possess. The VENs are located in insular cortex, corpus callosum, prefrontal cortex, anterior cingulate cortex, and columns of nerves (mini columns in the cortex support parallel processing. Large numbers of synapses are interconnected between nerve structures and the two sides of the brain (corpus callosum). This development, organization, and interconnection allows for complex social cognition, language, abstract thought, planning, ability to practice and teach, reasoning, and deception. The advanced re-organization of the human brain has given us these abilities, and many more that define res as human. However, it has come at a cost. The neuro-degenerative diseases such as Schizophrenia, Autism, and Alzheimer's. These diseases are as unique to humans as is advanced brain function. What specifically causes these problems is currently unknown.

All neurons work by essentially the same mechanism. When they are stimulated to a certain threshold, they fire and send an electro-chemical signal up the axon to the cell body. The body regulates this with proteins, chemicals, and substances—these are called ligands.

One of the leading theories is that there are excess concentrations of the neuroexcitatory substance glutamate in the developing brain and cerebrospinal fluid (CSF) of these afflicted children. Studies have shown it in varying levels of elevation in the brain, CSF, and blood of autistic children. There is a correlation between higher levels of glutamate and more severe autistic symptoms. This is believed to cause a condition called neuroexcitatory toxicity while the higher level structures are growing and interconnecting between 1.5 and 5 years of age. This can damage the developing, interconnecting neurons. The age of onset of the higher levels of glutamate, degree of levels above normal, genetic sensitivity to it, and area of the brain affected, could account for the vast spectrum of symptoms that are present in autism.

Substances that make nerves fire with less stimulation are called "excitatory." Substances that make nerves require more stimulation to fire are called "inhibitory." Examples of neuroexcitatory substances are nicotine, cocaine, methamphetamine, epinephrine, and glutamate. Examples of neuroinhibitory substances are serotonin, gamma-aminobutyric acid (GABA), narcotics, and other medications such as Lyrica (for nerve pain) and Valium (an anxiolytic/sedative). Too much inhibition of nerves can cause drowsiness and death. In contrast, too many excitatory compounds can cause nerves to fire much too fast with the possibility of resulting pain, lack of sleep, light sensitivity, cell death, seizures, etc. (symptoms depend on the function of the specific nerves).

Doctors have tried to get rid of these high levels of glutamate in the brains of autistic children by blocking its production or disabling glutamate receptors. This was not successful because glutamate is the most common neurotransmitter inside the brain (about 60%), and the side effects of the medications were too severe. The question is the origin of excess glutamate. Further question is how to get rid of it without affecting normal glutamate levels inside neurons and its normal functions. The excess glutamate in autistic children's blood, CSF, and brain is expected to come from the child being born with or developing migraines, fibromyalgia, or related neuropathic conditions between 1.5 and 5 years of age, when the higher functioning structures of the brain are forming. In adults with migraines, fibromyalgia, and neuropathic conditions the glutamate levels in the brain, blood, and CSF are elevated. Physical symptoms that can be observed on a toddler with ASD (autism) are the same as those of fibromyalgia, migraines, and neuropathic condition—light sensitivity, dilated pupils, sensitivity to loud noises, sleep disturbances, hyperactivity, sensitivity to touch, depression, and anxiety.

In migraines and fibromyalgia, the source of the overproduction of glutamate is believed to be the neurostructural cells that surround the neurons. They are the glial, satellite, and astrocyte cells. The mechanism is that substance P, CGRP (calcitonin gene-related peptide), and glutamate are produced intracellularly by the ribosomes of these cells, packaged in vesicles, and transported to the cell membrane. Here, a specialized protein called SNAP25 and/or VAMP transports it across the cell membrane and it is released into the CSF. They then act as ligands to the nerves and make them fire with less stimulation (neuroexcitation). The only other place the SNAP25 and/or VAMP is known to be functional in the human body is at the neuromuscular junction in muscle cells where it releases vesicles with acetylcholine into the neuromuscular junction and causes muscles to contract. In normal glutamate, substance P, and CGRP production in the cells, it is used internally in the neurons and not released by the SNAP25 and/or VAMP into the CS spaces.

In particular, the excess glutamate, substance P, and CGRP in the brain retards, damages, or causes malformation in the developing higher structures. Subcutaneous botulinum toxin injection or any other injection that allows the botulinum toxin to reach the unmyelinated sensory C fiber (e.g., intradermal injection, etc.) has been shown to lower the glutamate levels to normal in adult patients with migraines, fibromyalgia, and other neuropathic conditions.

Starting at birth, children can be tested for higher levels of substance P CGRP, and glutamate in their blood at routine checkups. If it is higher than normal and they show the physical symptoms and are not meeting developmental milestones, then they can be treated subcutaneously or by any other injection that allows the botulinum toxin to reach the unmyelinated sensory C fiber (e.g., intradermal injection, etc.) with botulinum toxin to reduce the excess glutamate and restore a normal developmental environment in the brain. The injected botulinum toxin will stop the overproduction of glutamate, substance P, CGRP, and the neuroexcitatory effects it produces in fibromyalgia, migraines, and other neuropathic conditions.

To diagnose ASD (autism), blood glutamate levels could be checked at regular doctor visits starting in infancy. Doctors should also make sure brain development milestones are being met. Physical symptoms are substantially the same in migraines, fibromyalgia, depression, ASD (autism), and other neuropathic disorders: a) light sensitivity (dilated pupils), b) sensitivity to loud noises, c) hyperactivity, d) sensitivity to touch (tight clothes, being held, etc.), e) stomach issues such as unexplained IBS.

If a patient is diagnosed to experience autism, they can be given botulinum toxin subcutaneously or by any other injection that allows the botulinum toxin to reach the unmyelinated sensory C fiber (e.g. intradermal injection, etc.) to prevent or alleviate related symptoms and/or blood tests to assess blood levels of substance P, CGRP, and glutamate. Then periodically developmental milestones and neuropathic symptoms are monitored as well as glutamate levels. Monitoring glutamate levels is important particularly for infants because it would be difficult to evaluate them for developmental milestones and neuropathic symptoms because of their age. Thus, the method will allow the doctors to know when botulinum toxin needs to be re-administrated. The botulinum toxin injection can be given to and/or around the vicinity of a trigeminal nerve, a cervical nerve, a thoracic nerve, a lumbar nerve, and/or a sacral nerve of the patient. The trigeminal nerve may include, but not be limited to, an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The cervical nerve may include, but not be limited to, a c-2 nerve, c-3 nerve, c-4 nerve, c-5 nerve, c-6 nerve, c-7 nerve, c-8 nerve and a combination thereof. For example, 2-4 units to and/or around the vicinity of an ophthalmic, maxillary, and/or mandibular nerve of the trigeminal nerve (bilateral), 2-4 units to and/or around the vicinity of c-2 to c-3, c-4 to c-6, and/or c-7 to c-8 of the cervical nerve, about one-inch lateral to the spine (bilateral), 2-4 units to and/or around the vicinity of t-2 to t-3, t-5 to t-6, t-7 to t-9, and/or t-10 to t-12 of the thoracic nerve, about one inch lateral to the spine (bilateral), 2-4 unit, to and/or around the vicinity of 1-1 to 1-2, 1-2 to 1-3, and/or 1-4 to 1-5 of the lumbar nerve, about one inch lateral to the spine (bilateral), and/or 2-4 units to and/or around the vicinity of s-1 to s-2, s-3 to s-4, and/or s-4 to s-5 of the sacral nerve, about one inch lateral to the spine (bilateral) can be administered. In one embodiment, 3 injections of 2 units each distributed along each side of the neck in the cervical area on the trigeminal nerve, 1 injection of 2 units in ophthalmic, maxillary, mandibular division subcutaneous bilaterally. These are adult dosages. The dosage for 0-5 year olds would have to be adjusted for age and weight.

Botulinum toxin is given to lower the levels of substance P, CGRP, and glutamate, and it normally begins to work after about three days, when given about to an inch from the spinal cord for all spinal injections. Many original studies gave it in the forearm or calf, and it takes about 2 weeks to begin working. When is given near the dorsal root ganglion; it normally takes 3 to 5 days and one to two weeks to reach the height of its effectiveness. That is because it is a shorter distance to diffuse up the axon to the cell body. Blood glutamate levels could be monitored to make sure that levels drop to normal, and physical symptoms monitored to make sure the normalize as well (developmental milestones charted). When the botulinum toxin wears off and blood tests show an increase in substance P, glutamate, or CGRP and/or the symptoms begins to re-develop, more botulinum toxin can be given to combat this effect. If levels/symptoms fail to normalize, then if desired, a small dose of one of the glutamate antagonists can be administered to help lower glutamate levels without producing side effects.

In general, the therapeutically effective dosage or amount can be between 1-150 units depending on their body weights. The dosage for adults whose weight is about 150 lbs. is about 50-150 units. For children over about 5 year olds at which brain formation has ceased, the dosage can be adjusted to their body weight. For example, for toddlers (from about 1 to 5 year olds), the dosage can be about 1-30 units. This is an estimate, but 30 units is the maximum dosage that has been used safely since the 1990s in cerebral palsy infants and young children to control their severe muscle spasms.

Treatment of Tolerance to Narcotics

One theory of the cause of tolerance is that narcotics inhibit the firing of neurons by acting on the opioid receptors, causing a decrease in sensory pain. Narcotics produce other symptoms when different functional nerves are inhibited, such as drowsiness, constipation, lethargy, euphoria, shallow breathing, forgetfulness, etc. In response to the system-wide depression and inhibition of neurons firing, the sensory nerves produce the neuroexcitatory substances (substance P, CGRP, and glutamate) to balance out the narcotic's inhibition of firing and depression of the nervous system. After the excitatory production is ramped up and the body returns to a more normal neural situation, the narcotics are no longer as effective so the patient has to take more narcotics to get the same effect. In result, the excitatory chemical production is increased and a vicious cycle results, with the patient taking more and more of the narcotics they rely on to relieve the mental pain, physical pain, or to maintain the euphoria they seek.

Chronic narcotic use causes the increased use of a narcotic to get the same desired effect that was previously attained with less medication due to the above tolerance mechanism. This results in the vast overproduction of the neuroexcitatory chemicals in the body's battle to try to return to a state of normal neural function. When a person runs out of the drug, is unable to obtain it, or decides to quit taking it, the extreme neuron inhibition (depression) of the firing of the body's neurons is suddenly gone. The continued vast overproduction of the neuroexcitatory substances caused by the narcotic usage tolerance effect results in symptoms of withdrawal, including alternating sweating and chills, diarrhea, nausea, rhinorrhea, shaking, tachycardia, uncontrollable yawning, lacrimation, sneezing, pupil dilation, restlessness, depression, migraines, anxiety, and pain.

If a patient is going to have to be on narcotics for extended periods of time, they can be given botulinum toxin to prevent tolerance and blood tests to assess base blood levels of substance P, CGRP, and glutamate. This should allow doctors to test for rising glutamate levels as well as clinical symptoms to tell if tolerance is developed. A new way to treat chronic pain is as follows. Baseline Glutamate levels are taken when narcotics are first administrated. Normal doses of narcotics are given to control pain as well as botulinum toxin into all sensory nerve areas. Then periodically symptoms of tolerance are monitored as well as glutamate levels. This will allow the doctors to know when botulinum toxin needs to be re-administrated. The glutamate test will also allow doctors to know when a patient is telling the truth about tolerance symptoms or lying to get more drugs for Euphoria or to sell. The subcutaneous botulinum toxin injection or any other injection that allows the botulinum toxin to reach the unmyelinated sensory C fiber (e.g., intradermal injection, etc.) can be given to and/or around the vicinity of a trigeminal nerve, a cervical nerve, a thoracic nerve, a lumbar nerve, and/or a sacral nerve of the patient. The trigeminal nerve may include, but not be limited to, an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The cervical nerve may include, but not be limited to, a c-2 nerve, c-3 nerve, c-4 nerve, c-5 nerve, c-6 nerve, c-7 nerve, c-8 nerve and a combination thereof. For example, 2-4 units to and/or around the vicinity of an ophthalmic, maxillary, and/or mandibular nerve of the trigeminal nerve (bilateral), 2-4 units to and/or around the vicinity of c-2 to c-3, to c-6 and/or c-7 to c-8 of the cervical nerve, about one-inch lateral to the spine (bilateral), 2-4 units to and/or around the vicinity of t-2 t-3, t-5 t-6, t-7 to t-9 and/or t-10 to t-12 of the thoracic nerve, about one inch lateral to the spine (bilateral), 2-4 unit to and/or around the vicinity of 1-1 to 1-2, 1-2 to 1-3, and/or 1-4 to 1-5 of the lumbar nerve, about one inch lateral to the spine (bilateral), and/or 2-4 units to and/or around the vicinity of s-1 to s-2, s-3 to s-4, and/or s-4 to s-5 of the sacral nerve, about one inch lateral to the spine (bilateral) can be administered. These are adult dosages. The dosage for 0-5 year olds would have to be adjusted for age and weight.

Botulinum toxin is given to maintain the levels of substance P, CGRP, and glutamate, and it normally begins to work after about three days. It normally takes for botulinum toxin about one to two weeks to reach the height of its effectiveness. Blood glutamate levels could be monitored to make sure that levels stay normal, and physical symptoms monitored to make sure they stay normal as well. When the botulinum toxin wears off and blood tests show an increase in substance P, glutamate, CGRP, or symptoms of tolerance, more botulinum toxin can be given to combat this effect. If levels/symptoms fail to normalize, then if desired, a small dose of one of the glutamate antagonists can be administered to help lower glutamate levels without producing side effects.

In general, the therapeutically effective dosage or amount can be between 1-150 units depending on their body weights. The dosage for adults whose weight is about 150 lbs. is about 50-150 units. For children over about 5 year olds at which brain formation has ceased, the dosage can be adjusted to their body weight. For example, for toddlers (from about 1 to 5 year olds), the dosage can be about 1-30 units. This is an estimate, but 30 units is the maximum dosage that has been used safely since the 1990s in cerebral palsy infants and young children to control their severe muscle spasms.

Treatment of Vestibular Vertigo

Vertigo is a symptom of several health conditions that can be described as spinning dizziness, disorientation, or an abnormal or false sensation of motion. It can be associated with other symptoms, such as nausea, sweating, headache, or difficulty walking, and is typically worse upon standing or when the head is moved.

There are many suspected causes of vertigo, including Meniere's disease, labyrinthitis, benign paroxysmal positional vertigo (BPPV), and other less likely causes such as brain tumors or injuries, stroke, migraines, toxin exposure, and uneven pressure in the middle ear. Although not wishing to be bound by a theory, it is suggested that one of the causes can be chronic overproduction of the neurostimulatory substances glutamate, substance P, and calcitonin gene-related peptide (GCRP) from a local damage to the vestibular nerves or from the central sensitization effect from depression, migraines, fibromyalgia, or other neuropathic condition. This results in a state of chronic hypersensitivity in the damaged and undamaged neurons (Vestibular Vertigo).

There are several known causes of vertigo, one of which can be associated with migraines. One of the widely accepted theories of the cause of migraines is the chronic or periodic overproduction of the neuroexcitatory substances. The overproduction of glutamate, substance P, and GCRP is produced by the neural structural cells (glial, satellite, and astrocyte). They cause hyperexcitation and sensitivity of the vestibular nerves so that they fire with minimal stimulation causing the symptom of vertigo. As described in the above paragraphs, subcutaneous botulinum toxin injection or any other injection that allows the botulinum toxin to reach the unimyelinated sensory C fiber (e.g., intradermal injection, etc.) can be used to effectively calm the overproduction of these substances for extended periods of time.

The problem is that the vestibular nerve is a cranial nerve and there is no superficial sensory exposure. It goes directly from the brain to the back side of the inner ear. However, there is an anastomotic connection between the cervical, trigeminal, and vestibular nerves. This is part of the visual tracking mechanism that prevents the head from moving side to side or rotating too quickly. The purpose of this is if head movement is too fast then there is too much visual information to process and it amounts to an image like that which pixelates on a television. This system, of course, can be voluntarily overridden if necessary by moving your head quickly, but while you are moving quickly your vision is not as sharp or clear.

Using this interconnection of the visual tracking system should allow botulinum toxin to be injected subcutaneously or by any other injection that allows the botulinum toxin to reach the unmyelinated sensory C fiber (e.g., intradermal injection, etc.) into the cervical and trigeminal nerves and reach the vestibular nerve and ganglia to calm its hypersensitivity.

The normal causes of vertigo are checked and of course treated if present, but if tests are negative and especially if they are present with other migraine, depression, and fibromyalgia, and other neuropathic conditions, symptoms such as headaches, light reaction, sensitivity to touch including the head, ears, or cervical or neck areas, depression, anxiety, and/or sleep disturbances, a blood glutamate test can be taken to see if it is elevated.

If a patient is diagnosed to experience vestibular vertigo, they can be given botulinum toxin subcutaneously or any other injection that allows the botulinum toxin to reach the unmyelinated sensory C fiber (e.g., intradermal injection, etc.) to prevent or alleviate related symptoms and if desired, blood tests to assess blood levels of substance P CGRP, and glutamate. The botulinum toxin injection can be given to and/or around the vicinity of a trigeminal nerve and/or a cervical nerve. The trigeminal nerve may include, but not be limited to, an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The cervical nerve may include, but not be limited to, a c-2 nerve, c-3 nerve, c-4 nerve, c-5 nerve, c-6 nerve, c-7 nerve, c-8 nerve and a combination thereof. For example, 2-4 units to and/or around the vicinity of an ophthalmic, maxillary, and/or mandibular nerve of the trigeminal nerve (bilateral) and/or 2-4 units to and/or around the vicinity of c-2 to c-3, c-4 to c-6, and/or c-7 to c-8 of the cervical nerve, about one-inch lateral to the spine (bilateral) can be administered. The bilateral injections are necessary even if the vertigo is in one ear because there is substantial crossover side to side in the trigeminal and cervical nerves. These are adult dosages. The dosage for 0-5 year olds would have to be adjusted for age and weight.

Botulinum toxin is given to lower the levels of substance P, CGRP, and glutamate, and it normally begins to work after about three days. It normally takes for botulinum toxin about one to two weeks to reach the height of its effectiveness. Blood glutamate levels could be monitored to make sure that levels drop to normal, and physical symptoms monitored to make sure they normalize as well. When the botulinum toxin wears off and blood tests show an increase in substance P, glutamate, or CGRP, the symptoms begins to redevelop, and more botulinum toxin can be given to combat this effect. If levels/symptoms fail to normalize, then if desired, a small dose of one of the glutamate antagonists can be administered to help lower glutamate levels without producing side effects.

In general, the therapeutically effective dosage or amount can be between 1-150 units depending on their body weights. The dosage for adults whose weight is about 150 lbs. is about 50-150 units. For children over about 5 year olds at which brain formation has ceased, the dosage can be adjusted to their body weight. For example, for toddlers (from about 1 to 5 year olds), the dosage can be about 1-30 units.

Treatment of Tinnitus

Tinnitus is defined as hearing sound when no external sound is present. Patients have often described tinnitus as a "ringing in the ears," though clicking, hissing, roaring, or more rarely, unclear voices or music can be heard. Patients may describe what they hear as loud or soft, high- or low-pitched, and may experience this in one or both ears. Tinnitus usually comes on gradually but may be more sudden depending on the cause. In some cases, tinnitus may become so severe that it can cause depression or anxiety and interfere with concentration.

Tinnitus is a symptom that can result from a number of underlying causes, rather than a disease itself. Conditions that can precipitate tinnitus are ear infections, noise-induced hearing loss, Bell's Palsy, brain tumors, neck injuries in the c1-c3 area, brain injuries, diseases of the heart or blood vessels, Meniere's disease, emotional stress, certain medications, or overproduction of earwax. It is more common in patients suffering from depression, and diagnosis of the symptom's origin is usually based on the patient's description.

When ear neurons are damaged or destroyed, there should be lessened or no ability to hear. Thus, it seems counterintuitive that a patient with damaged or destroyed ear neurons experiences the constant sound or even increased volume of sounds. Not wishing to be bound to a theory, tinnitus may stem from the overproduction of substance P, glutamate, and CGRP (calcitonin gene-related peptide). They are produced after injury to sensory neurons. These neuroexcitatory chemicals cause a state of hypersensitivity in the remaining cochlear neurons that cause them to fire with little or no stimulation.

For botulinum toxin to be effective, it must be injected near subcutaneous c-fibers which are not myelinated so it can soak into them and travel up to the cell bodies and exert its effect. The problem is the cochlear nerve is a cranial nerve that comes directly out of the brain and enters the ear with no superficial exposure. How do you reach the cochlear ganglia with the botulinum toxin? There is a system for sound location in animals that enables them to determine the direction and distance of a sound. The extreme examples are bats that can fly in the dark and catch insects at night in the air while flying, and whales and porpoises that use sound location under water (sonar). This system requires input from the cervical nerves c1-c3 and the trigeminal and facial nerve. These nerves move the neck, face, and ears to position the ears so sound origin can be located. To make this system work, they have branches that tie into (anastomosis) with the cochlear and vestibular nerves. They have superficial c-fibers that botulinum toxin can be injected into so it can reach the cochlear nerve. The botulinum toxin can be injected into them and travel to the cochlear ganglion and reduce the chronic neural excitation that is one of the causes of tinnitus. This has been shown clinically with botulinum toxin being injected subcutaneously or by any other injection that allows the botulinum toxin to reach the unmyelinated sensory C fiber (e.g., intradermal injection, etc.) where it will reduce or eliminate tinnitus from this cause.

To diagnose tinnitus, blood glutamate levels and physical symptoms could be checked at regular doctor visits. Physical symptoms may include, but not limited to, an intermittent or continuous noise in the ears, such as ringing, roaring, buzzing, hissing, or whistling.

If a patient is diagnosed to experience tinnitus, they can be given botulinum toxin subcutaneously or by any other injection that allows the botulinum toxin to reach the unmyelinated sensory C fiber (e.g., intradermal injection, etc.) to prevent or alleviate related symptoms and/or blood tests to assess blood levels of substance P, CGRP, and glutamate. The botulinum toxic injection can be given to and/or around the vicinity of a trigeminal nerve and/or a cervical nerve of the patient. The trigeminal nerve may include, but not be limited to, an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The cervical nerve may include, but not be limited to, a c-2 nerve, c-3 nerve, c-4 nerve, c-5 nerve, c-6 nerve, c-7 nerve, c-8 nerve and a combination thereof. For example, 2-4 units to and/or around the vicinity of an ophthalmic, maxillary, and/or mandibular nerve of the trigeminal nerve (bilateral) and/or 2-4 units to and/or around the vicinity of c-2 to c-3, c-4 to c-6, and/or c-7 to c-8 of the cervical nerve, about one inch lateral to the spine (bilateral) can be administered. The bilateral injections are necessary even if the tinnitus is in one ear because there is substantial crossover side to side in the trigeminal and cervical nerves. These are adult dosages. The dosage for 0-5 year olds would have to be adjusted for age and weight.

Botulinum toxin is given to lower the levels of substance P, CGRP, and glutamate, and it normally begins to work after about three days. It normally takes for botulinum toxin about one to two weeks to reach the height of its effectiveness. Blood glutamate levels could be monitored to make sure that levels drop to normal, and physical symptoms monitored to make sure they normalize as well. When the botulinum toxin wears off and blood tests show an increase in substance P, glutamate, or CGRP, the symptoms begins to redevelop, and more botulinum toxin can be given to combat this effect. If levels/symptoms fail to normalize, then if desired, a small dose of one of the glutamate antagonists can be administered to help lower glutamate levels without producing side effects.

In general, the therapeutically effective dosage or amount can be between 1-150 units depending on their body weights. The dosage for adults whose weight is about 150 lbs. is about 50-150 units. For children over about 5 year olds at which brain formation has ceased, the dosage can be adjusted to their body weight. For example, for toddlers (from about 1 to 5 year olds), the dosage can be about 1-30 units.

A New Clinical Method for Treating the Symptoms and Causes of Anxiety and/or Depression Subcutaneous botulinum toxin or any other injection that allows the botulinum toxin to reach the unmyelinated sensory C fiber (e.g., intradermal injection, etc.) can stop or minimize symptoms of depression and/or anxiety. Though not wishing to be bound by any particular theory, depression and/or anxiety is believed to be associated with increased glutamate levels. The glutamate levels can be increased by either mental injury (trauma) or medical injury. Botulinum toxin is given first to help or stop symptoms so that an appropriate processional such as a doctor can conduct psychoanalysis or medical examination to assess which caused the increase of the glutamate level of a patient. If the patient turns out to have a mental injury after psychoanalysis, proper mental therapy may be provided to help the patient deal with mental injury. If the patient turns out to have a medical injury after medical examination, then medical treatment is provided to prevent increasing the glutamate level. Physical symptoms could be also checked. They may include, but not limited to, changes in sleep, appetite, energy level, concentration, daily behavior or self-esteem, or thoughts of suicide.

If a patient is diagnosed to have depression and/or anxiety, they can be given botulinum toxin to reduce or eliminate symptoms of anxiety and/or depression and/or blood tests to assess blood levels of substance P, CGRP, and glutamate. The botulinum toxin injection can be given to and/or around the vicinity of a trigeminal nerve, a cervical nerve, a thoracic nerve, a lumbar nerve, and/or a sacral nerve of the patient. The trigeminal nerve may include, but not be limited to, an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The cervical nerve may include, but not be limited to, a c-2 nerve, c-3 nerve, c-4 nerve. c-5 nerve, c-6 nerve, c-7 nerve, c-8 nerve and a combination thereof. For example, 2-4 units to and/or around the vicinity of an ophthalmic, maxillary, and/or mandibular nerve of the trigeminal nerve (bilateral), 2-4 units to and/or around the vicinity of c-2 to c-3, c-4 to c-6, and/or c-7 to c-8 of the cervical nerve, about one-inch lateral to the spine (bilateral), 2-4 units to and/or around the vicinity of t-2 to t-3, t-5 to t-6, t-7 to t-9, and/or t-10 to t-12 of the thoracic nerve, about one inch lateral to the spine (bilateral), 2-4 unit to and/or around the vicinity of 1-1 to 1-2, 1-2 to 1-3, and/or 1-4 to 1-5 of the lumbar nerve, about one inch lateral to the spine (bilateral), and/or 2-4 units to and/or around the vicinity of s-1 to s-2, s-3 to s-4, and/or s-4 to s-5 of the sacral nerve, about one inch lateral to the spine (bilateral) can be administered. These are adult dosages. The dosage for 0-5 year olds would have to be adjusted for age and weight.

Botulinum toxin is given to lower the levels of substance P, CGRP, and glutamate, and it normally begins to work after about three days. It normally takes for botulinum toxin about one to two weeks to reach the height of its effectiveness. Blood glutamate levels could be monitored to make sure that levels drop to normal, and physical symptoms monitored to make sure they normalize as well. Normal blood glutamate levels may range from 40 to 60 uM. Alternatively, normal blood glutamate levels may be one a person skilled in the art would reasonably perceive. When the botulinum toxin wears off and blood tests show an increase in substance P, glutamate, or CGRP, the symptoms begins to redevelop, and more botulinum toxin can be given to combat this effect. If levels/symptoms fail to normalize, then perhaps a small dose of one of the glutamate antagonists or antidepressants can be administered to help lower glutamate levels without producing side effects. If they cannot be cured, then botulinum toxin is continued to minimize or eliminate symptoms indefinitely.

In general, the dosage can be between 1-150 units depending on their body weights. The dosage for adults whose weight is about 150 lbs. is about 50-150 units. For children over about 5 year olds at which brain formation has ceased, the dosage can be adjusted to their body weight.

Botulinum toxins for use according to the present invention can be stored in lyophilized, vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or to the vicinity of the aforementioned nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin effects neural systems believed to be involved in a selected neuropsychiatric disorder, and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor), and/or a translocation domain). By way of example, and not by way of limitation, a fragment of a botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

The botulinum toxin is selected from the group consisting of botulinum toxin type A, botulinum toxin type 13, botulinum toxin type C, botulinum toxin type D, botulinum toxin type E, botulinum toxin type F, botulinum toxin type G, a fragment thereof, a hybrid thereof, a chimera thereof, and a combination thereof. Because of different mechanisms and cleavage sites of botulinum toxins, a potency, a dosage, or a duration nay vary depend on the type of botulinum toxins. The botulinum toxin can be used with other modulating drugs or chemicals. In further embodiments, the therapeutically effective amount of the botulinum toxin administered is between about 1 unit and about 150 units.

The present invention will now be explained in details with reference to examples.

EXAMPLE 1

A 40-year-old female patient experienced the following neuropathic symptoms: chronic, severe post shingles pain on the left side from c-7 to t-4, chronic migraine headaches, trigeminal neuralgia, tinnitus, chronic Dry Eye Syndrome (DES) since Lasik surgery 4 years ago, sleep disturbances (sleeps 3-4 hours then wakes up and cannot go back to sleep), chronic fatigue, anxiety, depression, and pain and muscle spasms in the neck, shoulder, and upper back. The patient was taking the following medications: Tegretol for trigeminal neuralgia, Gabapentin for shingles, and Lexapro for depression. These medications alleviated her symptoms some, but not much. Then, she was administered botulinum toxin type A, all injections subcutaneous: 2-4 units in ophthalmic, maxillary, and mandibular dermatome of the trigeminal nerve (bilateral); and 4 units in c-2, c-4, c-6, t-2, t-4, and t-6, about one inch to the side of the spine (bilateral).

All of her symptoms started to subside by day 5 and were gone by day 14, and the patient was able to get off all her medications. All the symptoms including the Dry Eye Syndrome stayed gone for about 4 months, at which time they all started to return, including the Dry Eye Syndrome. When she received botulinum toxin again, all her symptoms again went away, including her Dry Eye Syndrome.

EXAMPLE 2

A 25-year-old Autistic female experienced moderate to severe ASD (autism). The subject was diagnosed with Pervasive Developmental Disorder at age 2. She also has Agenesis of the Corpus Callosum (ACC), Attention Deficit Disorder (ADD) and Obsessive Compulsive Disorder (OCD). During her young life, she was prescribed Ritalin to help keep her focused. She also took Zoloft to help control her anxiety. She completed school as a special needs student in the life skills class through age 22. After years of being medicated and experiencing high and low emotional episodes, the family decided to cease medication. The subject's conversations were more about expressing wants and/or needs, never conversational. The last day of the prescribed medication was taken Dec. 27, 2018.

On Jul. 17, 2019, she received multiple shots of botulinum toxin in her trigeminal & cervical dermatomes: 3 injections of 2 units each distributed along each side of the neck in the cervical area on the trigeminal nerve, 1 injection of 2 units in ophthalmic maxillary, mandibular division subcutaneous bilaterally. No immediate changes were observed.

After about two weeks, she became more conversational and aware about her surroundings. She also did not show any mood swings that she had sometimes showed. She still showed a few OCD moments, such as slamming the toilet seat cover, slamming the doors, and slamming the refrigerator door. Her mother reported that there was definitely a progress.

After another week, she started to sleep much better. She also proactively showed more sociable behaviors with proper responses to her external environment. She verbalized more about her situations and behaved independently and properly. She even remembered and conversed the details of past events.

Overall, she was significantly more in tune with her surroundings. She showed significant improvement in her behavior, emotion and verbal ability. Now, she is enjoying her life in a much more independent and autonomous fashion. The female patient in the case study weighed about 150 lbs. The dosage to a toddler that weighs about 25 lbs. can be adjusted to their body weight.

EXAMPLE 3

A 62-year-old female patient experienced severe intractable vertigo. Her vertigo symptoms were so severe that she spent most of her day lying down with as little head movement as possible because the spinning and nausea were so severe. Riding in a car was extremely difficult for her. It was necessary for her to stop and throw up periodically. She had been to numerous doctors, tried numerous specialists, tried numerous medications, and even had surgery to try to control it to no avail. She presented with severe nausea, vertigo, light sensitivity, and moderate hypersensitivity to touch to her right ear/temple area and posterior to her ear. Her diagnosis was a possible vestibular vertigo. Accordingly, subcutaneous botulinum toxin was injected—2-4 units in the ophthalmic, maxillary, and mandibular areas of the trigeminal nerve bilaterally; and 2-4 units in the c-2 to c-3 area, 2-4 units in the c-4 to c-5 area, and 2-4 units in c-6 to c-7 bilaterally.

Within 2 weeks, she reported 95% of her vertigo and nausea symptoms were gone, and she could walk unaided and ride in a car without symptoms. Some slight vertigo still existed if she moved her head back and forth too rapidly. The botulinum toxin A usually lasts for 3-4 months. She got new injections at approximately 2.5 months because she did not want it to come back.

EXAMPLE 4

Patient is a 49-year-old male. He suffers from chronic severe lumbar, sacral, and sometimes cervical pain. He also has protein S deficient and takes Eloquis for the resulting blood clots. The protein S deficiency may contribute to his chronic pain. He has been to numerous doctors for operations and steroid injection with only temporary help for his pain. In February, one of his orthopedic doctors told him the 6-Vicodin be was taking daily was too much and be needed to stop taking it or be was going to become addicted. So he did and for several weeks be experienced moderate to severe withdrawal pain, which be described as "rough." He staved off for about a month, but then decided pain was affecting him too much and starting taking 3 a day. At first be got about 5-6 hours relief from pain with each tablet depending if be did too much physical activity. After 6-8 weeks the effectiveness of the tablets started to decline. In July they were only effective for 2-3 hours. On August 21st, be received subcutaneous botulism toxin-12 units in Trigeminal, 12 units cervical, 12 units thoracic, 12 units Lumbar, and 12 center in sacral area for 60 units total. At day 5 after the injection, be started noticing that they seemed to be lasting longer. By day 10 they were lasting up to 6 hours.

Unless defined otherwise, all technical and scientific terms used herein have same meaning as commonly understood by the person of ordinary skill in the art to which this invention belongs. Thus the scope of the embodiments of the present invention should be determined by the appended claims and their legal equivalents.

What is claimed is:

1. A method of treating tolerance to narcotics in a patient in need thereof who is necessitated to be on long term narcotic use, comprising administering a botulinum toxin to the patient, thereby treating the tolerance to narcotics, wherein the administering for an adult comprises by subcutaneous or intradermal injection 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the spine, 2-4 units to and/or around the vicinity of a lumbar nerve, lateral to the spine, and 2-4 units to and/or around the vicinity of a sacral nerve, lateral to the spine.

2. The method of claim 1, wherein the trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof.

3. The method of claim 1, wherein the cervical nerve is selected from the group consisting of a c-2 nerve, c-3 nerve, c-4 nerve, c-5 nerve, c-6 nerve, c-7 nerve, c-8 nerve and a combination thereof.

4. The method of claim 1, wherein the botulinum toxin is selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, and a combination thereof.

5. The method of claim 1, wherein each of the subcutaneous or intradermal injection is bilateral.

6. The method of claim 1 wherein tolerance to narcotics in the patient is reduced.

7. The method of claim 1, wherein a total dosage of the botulinum toxin for an adult who weighs about 150 lbs is between about 50 and about 150 units.

8. The method of claim 7, wherein a total dosage of the botulinum toxin for an adult, a child over about 5 years old and a toddler about from 1 to 5 years old is adjusted for age, weight or a combination thereof.

9. The method of claim 1, wherein the thoracic nerve is selected from the group consisting of a t-2 nerve, t-3 nerve, t-5 nerve, t-6 nerve, t-7 nerve, t-8 nerve, t-9 nerve, t-10 nerve, t-11 nerve, t-12 nerve and a combination thereof.

10. The method of claim 1, wherein the lumbar nerve is selected from the group consisting of a 1-1 nerve, 1-2 nerve, 1-3 nerve, 1-4 nerve, 1-5 nerve and a combination thereof.

11. The method of claim 1, wherein the sacral nerve is selected from the group consisting of a s-1 nerve, s-2 nerve, s-3 nerve, s-4 nerve, s-5 nerve and a combination thereof.

* * * * *